United States Patent [19]

Wilk

[11] Patent Number: 5,304,117
[45] Date of Patent: Apr. 19, 1994

[54] CLOSURE METHOD FOR USE IN LAPAROSCOPIC SURGERY

[76] Inventor: Peter J. Wilk, 185 West End Ave., New York, N.Y. 10023

[21] Appl. No.: 982,394

[22] Filed: Nov. 27, 1992

[51] Int. Cl.$^5$ .................................. A61M 31/00
[52] U.S. Cl. .................................. 604/49; 604/93; 604/96; 604/265; 606/213
[58] Field of Search .............. 604/48, 49, 51, 54, 604/57, 93, 96, 171, 174, 175, 265, 278, 285; 606/213, 215, 195

[56] References Cited

U.S. PATENT DOCUMENTS

| | | |
|---|---|---|
| 2,701,559 | 2/1955 | Cooper . |
| 3,253,594 | 7/1963 | Matthews et al. .............. 604/96 |
| 3,483,859 | 12/1969 | Pittman . |
| 4,441,495 | 4/1984 | Hicswa . |
| 4,638,803 | 1/1987 | Rand . |
| 4,685,447 | 8/1987 | Iversen et al. . |
| 4,693,243 | 9/1987 | Buras . |
| 4,733,665 | 3/1988 | Palmaz . |
| 4,790,313 | 12/1988 | Borrelly . |
| 4,823,815 | 4/1989 | Watson et al. . |
| 4,854,316 | 8/1989 | Davis .................... 604/175 X |
| 5,007,900 | 4/1991 | Picha et al. .................. 604/106 |
| 5,092,841 | 3/1992 | Spears . |
| 5,092,850 | 3/1992 | Buma ........................ 604/175 |
| 5,125,897 | 6/1992 | Quinn et al. .................. 604/99 |
| 5,176,692 | 1/1993 | Wilk et al. . |
| 5,192,302 | 3/1993 | Kensey et al. .............. 606/213 |
| 5,246,441 | 9/1993 | Ross et al. .................. 606/53 |

FOREIGN PATENT DOCUMENTS

| | | |
|---|---|---|
| 2659440 | 7/1977 | Fed. Rep. of Germany . |
| 3837779 | 5/1989 | Fed. Rep. of Germany . |
| 9001969 | 3/1990 | World Int. Prop. O. . |

Primary Examiner—C. Fred Rosenbaum
Assistant Examiner—Corrine Maglione
Attorney, Agent, or Firm—R. Neil Sudol; Henry D. Coleman

[57] ABSTRACT

A method for use in laparoscopic surgery comprises the steps of disposing a laparoscopic trocar sleeve in an abdominal wall of a patient so that the sleeve traverses an opening in an abdominal skin surface of the patient and also traverses an underlying aperture in a peritoneum of the patient and providing a closure device having an elongate shaft and a distal end portion made of bioabsorbable material. The trocar sleeve is removed from the abdominal wall of the patient and at least part of the closure device is inserted through the skin surface opening so that the distal end portion of the closure device is partially disposed proximately to the aperture in the peritoneum. The skin surface opening is at least partially closed subsequently to the removal of the trocar sleeve and the insertion of the closure device. The closure device is maintained in a position at least partially traversing the abdominal wall of the patient so that the distal end portion of the closure device remains partially disposed proximately to the aperture so as to block entry of an abdominal organ into the aperture subsequently to the closure of the opening in the skin surface.

15 Claims, 2 Drawing Sheets

CLOSURE METHOD FOR USE IN LAPAROSCOPIC SURGERY

BACKGROUND OF THE INVENTION

This invention relates to a method for use during a laparoscopic surgical procedure. More particularly, this invention relates to a closure technique for use during a laparoscopic surgical procedure.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Laparoscopic surgery is frequently performed to remove a malfunctioning organ such as a gall bladder filled with stones. Generally, a severed bladder is removed from the patient's abdomen by drawing the organ against the distal end of the trocar sleeve and then withdrawing the trocar sleeve with the bladder entrained thereto.

Occasionaly, a complication resulting from laparoscopic surgery is a hernia. A portion of bowel becomes wedged in an aperture left in the peritoneum of the patient upon withdrawal of the trocar sleeve. A need exists for a method to prevent or obviate hernias resulting from laparoscopic surgery.

OBJECTS OF THE INVENTION

An object of the present invention is to provide a method for use in laparoscopic surgery which reduces, if not eliminates, the subsequent incidences of hernias.

Another, more particular, object of the present invention is to provide a laparoscopic closure technique for use in closing abdominal openings formed during laparoscopic surgery by trocars and associated sleeves.

A further particular object of the present invention is to provide such a method which is relatively easy to execute.

These and other objects of the present invention will be apparent from the drawings and detailed descriptions herein.

SUMMARY OF THE INVENTION

A method for use in laparoscopic surgery comprises the steps of (a) disposing a laparoscopic trocar sleeve in an abdominal wall of a patient so that the sleeve traverses an opening in an abdominal skin surface of the patient and also traverses an underlying aperture in a peritoneum of the patient, (b) providing a closure device having an elongate shaft and a distal end portion made of bioabsorbable material, (c) removing the trocar sleeve from the abdominal wall of the patient, (d) inserting at least part of the closure device through the skin surface opening so that the distal end portion of the closure device is partially disposed proximately to the aperture in the peritoneum, (e) at least partially closing the skin surface opening subsequently to the removal of the trocar sleeve and the insertion of the closure device, and (f) maintaining the closure device at least partially traversing the abdominal wall of the patient so that the distal end portion of the closure device remains partially disposed proximately to the peritoneal aperture so as to block entry of an abdominal organ into the aperture subsequently to the closure of the opening in the skin surface.

Pursuant to another feature of the present invention, the distal end portion of the closure device includes an expandable element and the method further comprises the step of expanding the expandable element after the closure device is inserted through the opening in the skin surface of the patient. Preferably, the expandable element is a balloon which is inflated upon insertion of the closure device into the abdominal wall.

According to a further feature of the present invention, the shaft of the closure device is severed at a point between the skin surface opening and the peritoneal aperture prior to the closure of the skin surface opening. Where the distal end portion of the closure device includes an expandable element, that element is preferably expanded prior to the severing of the shaft of the closure device.

According to a particular feature of the present invention, the insertion of the closure device is performed prior to the removal of the trocar sleeve. More particularly, the closure device is inserted into the trocar sleeve so that a proximal end segment of the shaft remains outside the patient.

According to another particular feature of the present invention, the removal of the trocar sleeve is implemented by grasping the proximal end segment of the closure device shaft and simultaneously pulling the trocar sleeve from the abdominal wall of the patient.

Pursuant to another feature of the present invention, a part of the shaft of the closure device (e.g., a head on the shaft) remains outside of the patient upon closure of the opening in the patient's abdominal skin surface.

A method in accordance with the present invention for use in laparoscopic surgery reduces, if not eliminates, the incidence of hernias at trocar sleeve insertion sites. The method is relatively easy to execute.

DETAILED DESCRIPTION

Figure 1:
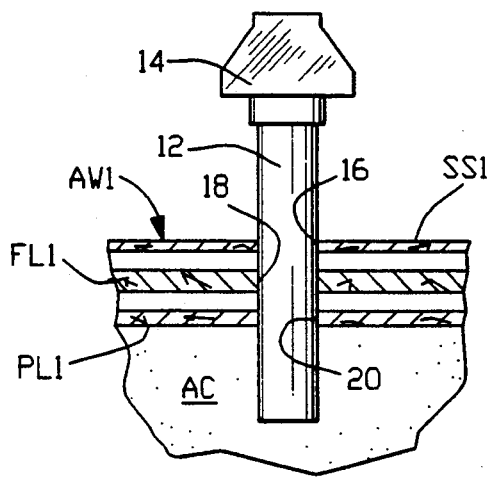
FIG. 1 is partially a cross-sectional view of an abdominal wall of a patient and partially a schematic side elevational view of a trocar sleeve traversing the abdominal wall.

As illustrated in FIG. 1, in a laparoscopic surgical procedure a trocar sleeve 12 provided at a proximal end with a schematically represented port element 14 is disposed in an abdominal wall AW1 of a patient so that the sleeve traverses an opening 16 formed in a skin surface SS1, a hole 18 formed in a fascia layer FL1, and an aperture 20 formed in an underlying peritoneum layer PL1 of a patient P. The distal end of trocar sleeve 12 projects into an abdominal cavity AC of the patient. At the onset of the laparoscopic procedure, trocar sleeve 12 is inserted with the aid of a trocar (not shown) upon insufflation of abdominal cavity AC with a Veress needle (not shown).

In order to effectively close aperture 20 to prevent a hernia due to intestine or another internal organ creeping into aperture 20 after the termination of the laparoscopic procedure, a distal end portion 22 of a closure device 24 is positioned in the abdominal hole defined by opening 16, hole 18 and aperture 20. Distal end portion 22 of closure device 24 comprises an inflatable balloon 26 made of a bioabsorbable material. Inflatable balloon 26 is mounted to a tubular shaft 28 also made of a bioabsorbable material. Balloon 26 communicates via shaft 28 with a source 30 of pressurized carbon dioxide, saline solution or another biocompatible fluidic agent.

Figure 2:
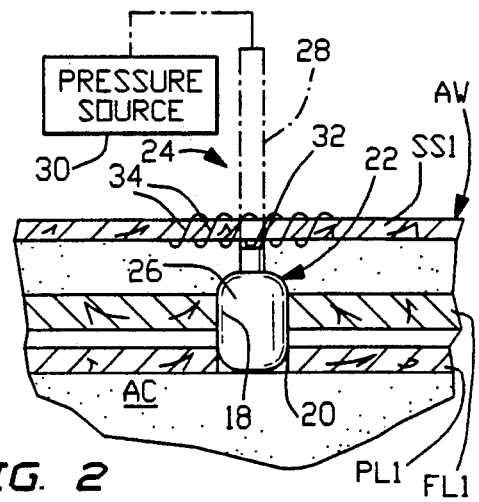
FIG. 2 is partially a cross-sectional view of the abdominal wall of FIG. 1, on a larger scale, and partially a schematic side elevational view of a closure device positioned, in accordance with the present invention, in a hole vacated upon removal of the trocar sleeve of FIG. 1.

Upon the removal of trocar sleeve 12 from abdominal wall AW1 at the termination of a laparoscopic procedure, distal end portion 22 of closure device 24 is inserted through opening 16 in skin surface SS1 so that distal end portion 22 is partially disposed proximately to aperture 20 in peritoneum PL1. During the insertion of distal end portion 22 of closure device 24, balloon 26 is in a deflated state. Upon a proper positioning of balloon 26 via shaft 28, pressure source 30 is connected to balloon 26 (e.g., via a non-illustrated valve) to inflate the balloon as shown in FIG. 2. Subsequently, a proximal end portion of shaft 28 is severed at 32, below skin surface SS1. Opening 16 is then closed with sutures 34.

Upon inflation, balloon 26 is maintained in a position at least partially traversing abdominal wall AW1 so that distal end portion 22 remains partially disposed proximately to aperture 20 so as to block entry of an abdominal organ (not shown into the aperture subsequently to the closure of opening 16 in skin surface SS1.

Figure 3A:
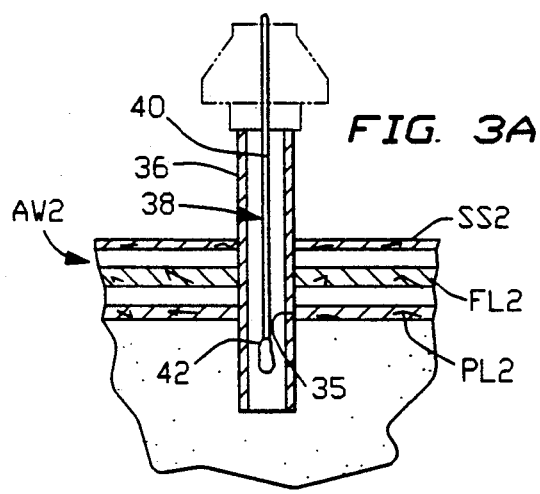
FIGS. 3A-3D are partially cross-sectional views, on different scales, of an abdominal wall and partially schematic side elevational views showing successive steps in a positioning of a closure device at the end of a laparoscopic surgical procedure in accordance with the present invention.
Figure 3B:
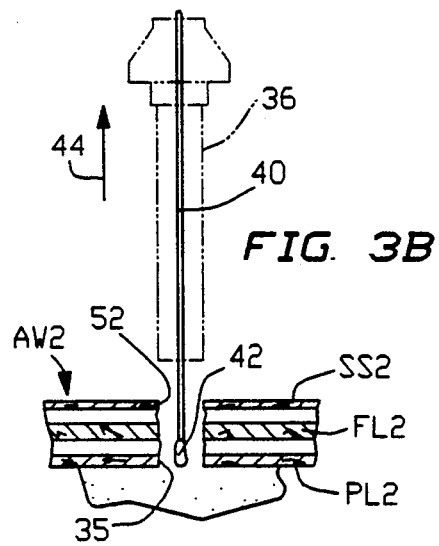

FIGS. 3A-3D illustrate an equivalent method for the closure of an aperture 35 formed in a pertoneal layer PL2 of an abdominal wall AW2 by a trocar sleeve 36. A closure device 38 comprising a tubular shaft 40 and a deflated balloon 42 is inserted through sleeve 36 so that balloon 42 is located inside the sleeve approximately at the level of abdominal wall AW2 (FIG. 3A). Trocar sleeve 26 is then removed from abdominal wall AW2, as indicated by an arrow 44 in FIG. 3B, while balloon 42 is maintained at the same level.

Figure 3C:
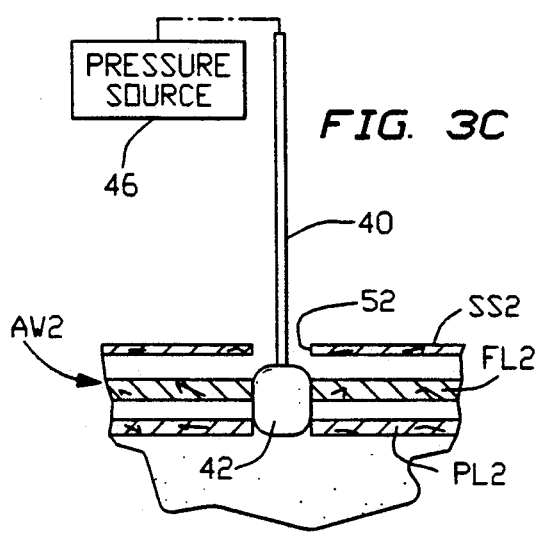
Figure 3D:
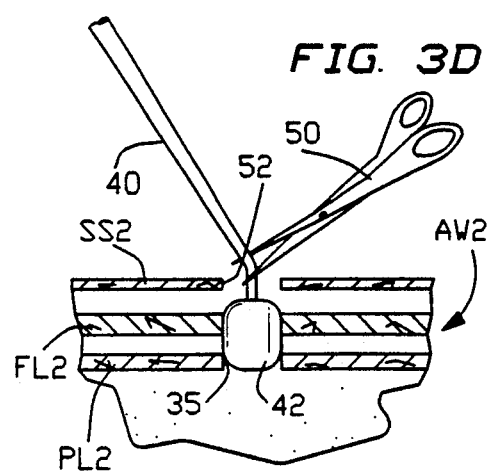

Upon the removal of sleeve 26 from abdominal wall AW2, tubular shaft 40 is connected to a pressure source 46, e.g., a hypodermic type syringe, as illustrated in FIG. 3C. Pressure source 46 is activated to inflate balloon 42, thereby blocking access to aperture 35 in peritoneal layer PL2. Upon the pressurization of balloon 42, shaft 40 is severed below a skin surface SS2 of abdominal wall AW2 through utilization of a cutting forceps 50, as illustrated in FIG. 3D. The cutting action also serves to crimp shaft 40 closed and prevent the escape of pressurizing fluid from balloon 42. Alternatively, shaft 40 may be provided at balloon 42 with a one-way valve (not shown) for preventing the exit of pressurizing fluid from balloon 42 upon the expansion thereof. Balloon 42, as well as at least a distal end portion of shaft 40, is made of a bioabsorbable material, as discussed hereinabove with reference to FIG. 2.

Upon the severing of shaft 40, an opening 52 in skin surface SS2 is closed, for example, by sutures or staples. Balloon 42 remains inflated long enough to prevent the insertion of intestinal loops through aperture 35 while the organic tissues of skin surface SS2, a fascia layer FL2 and peritoneal layer PL2 are healing. Subsequently, balloon 42 and the distal end portion of shaft 40 are absorbed into the patient's body.

Figure 4A:
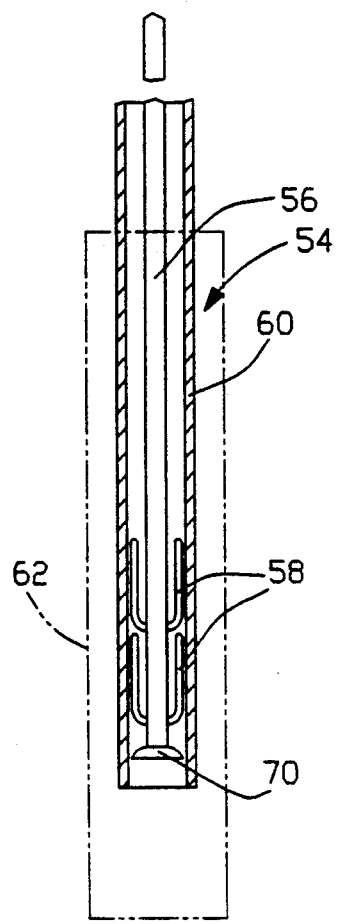
FIG. 4A is a side elevational view, partially in cross-section, of another closure device for use in a method in accordance with the present invention.

FIG. 4A shows another closure device 54 for possible use in the methods described hereinabove with reference to FIGS. 2 and 3A-3D. Closure device 54 comprises a central shaft 56 to which a plurality of fingers or spokes 58 are fixed. Shaft 56 is inserted inside a tube 60 so that spokes 58 are bent into a roughly parallel configuration with respect to shaft 56 and tube 60. Tube 60 thus serves as a temporary retainer for holding spokes 58 in a collapsed configuration in opposition to spring biasing forces tending to return spokes 58 to a radial configuration shown in FIG. 4B. Spokes 58 and at least a distal end portion of shaft 56 are made of a bioabsorbable material.

Upon the removal of a trocar sleeve 62 (FIG. 4A) from an aperture 64 (FIG. 4B) in a peritoneal layer PL3, a hole 66 in a fascia layer FL3, and an opening 68 in an overlying skin surface or layer SS3, a distal end of closure device 54 is inserted through opening 68 so that a distal tip or head 70 of shaft 56 is disposed at the level of peritoneal layer PL3. Tube 60 is then removed from about shaft 56, allowing spokes 58 to expand into the radial configuration of FIG. 4B wherein the spokes are inserted into and/or between layers SS3, FL3 and PL3, thereby holding shaft 56 and spokes 58 of closure device 54 in position to prevent the entrance of intestinal and other organ parts through aperture 64. Subsequently to the expansion of spokes 58 and the proper disposition of shaft 56 relative to hole 66, opening 68 and aperture 64, shaft 56 is severed below skin surface or layer SS3 and opening 68 is closed via sutures or staples 70.

Figure 4B:
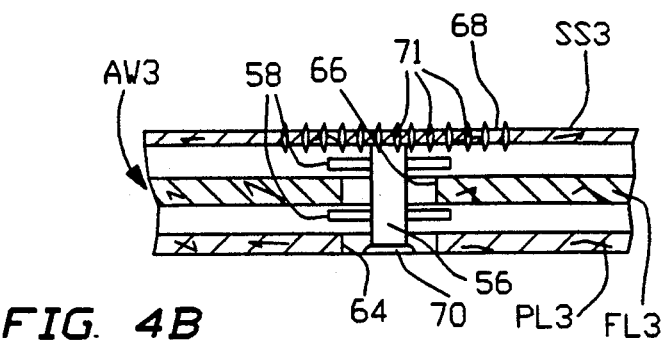
FIG. 4B is partially a cross-sectional view of an abdominal wall of a patient and partially a schematic side elevational view of a distal end portion of the closure device of FIG. 4B, upon deployment thereof in a trocar sleeve hole in an abdominal wall of a patient.

The device of FIGS. 4A and 4B can also be used in a method according to FIGS. 3A-3D wherein shaft 56 and optionally tube 60 are sufficiently long to enable the insertion of the distal end portion thereof into trocar sleeve 62 and the removal of the sleeve from the patient while shaft 56 is grasped to maintain proper positioning thereof. In this procedure, shaft 56 (and optionally tube 60) is grasped first at a proximal end during removal of sleeve 62 from the abdominal wall AW3 (see FIG. 4B) of the patient. Subsequently, if sleeve 62 is to be removed from around shaft 56 prior to the severing thereof, shaft 56 and tube 60 may be grasped at a median point.

Figure 5:
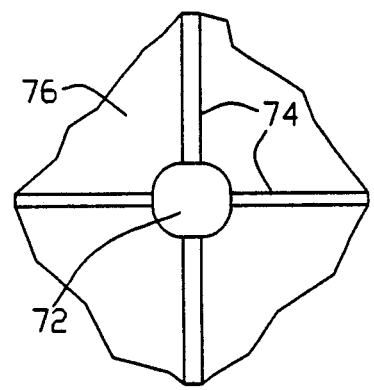
FIG. 5 is a bottom view of another closure device for use in a method in accordance with the present invention.

As depicted in FIG. 5, another closure device for use in the method described hereinabove with reference to FIG. 2 or FIGS. 3A-3D includes a shaft 72 to which a plurality of spokes or radial ribs 74 are attached in one or more spaced arrays (as in FIGS. 4A and 4B). A flexible web 76 is attached to spokes or ribs 74. A distal end portion of shaft 72, ribs 74 and web 76 are made of a bioabsorbable material. The closure device of FIG. 5 is inserted into a retainer tube such as tube 60 of FIG. 4A for installation in a patient's abdominal wall at the end of a laparoscopic procedure.

Figure 6:
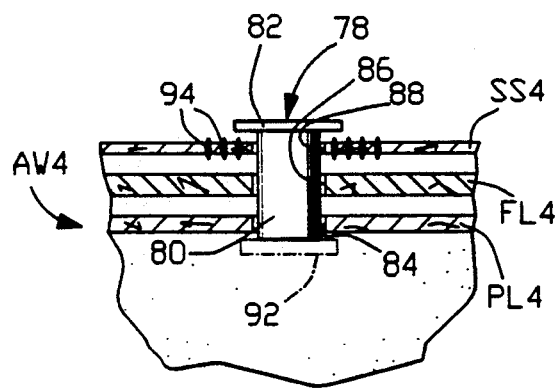
FIG. 6 is partially a cross-sectional view of an abdominal wall of a patient and partially a schematic side elevational view of a closure device upon deployment thereof in a trocar sleeve hole in the abdominal wall in accordance with the present invention.

FIG. 6 shows yet another closure device 78 for use in the method described hereinabove with reference to FIG. 2. Closure device 78 is in the form of a tube or shaft 80 with a head 82. Upon the withdrawal or extraction of a trocar sleeve (not shown in FIG. 6) from an abdominal wall AW4 and particularly from an aperture 84 in a peritoneal layer PL4, a hole 86 in a fascia layer FL4, and an opening 88 in an overlying skin surface or layer SS4, shaft 80 of closure device 76 is inserted through opening 88 so that a distal tip 90 of shaft 78 is disposed at the level of peritoneal layer PL4 and so that head 82 remains outside skin surface SS4. Opening 88 is then partially closed, e.g., with sutures or staples 94. Subsequently, after some healing and tissue growth has occurred, head 82 may be severed from shaft 78 and opening 88 completely closed. Shaft 80 may be provided at a free end with a flange or head 92 for facilitating the blocking function of closure device 78.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in laparoscopic surgery, comprising the steps of:
    disposing a laparoscopic trocar sleeve in an abdominal wall of a patient so that said sleeve traverses an opening in an abdominal skin surface of the patient and also traverses an underlying aperture in a peritoneum of the patient;
    providing a closure device having an elongate shaft, said closure device also having a distal end portion made of bioabsorbable material;
    removing said sleeve from the abdominal wall of the patient;
    inserting at least part of said closure device through said opening so that said distal end portion is partially disposed proximately to said aperture;
    at least partially closing said opening subsequently to said steps of removing and inserting; and
    subsequently to said step of closing, maintaining said closure device at least partially traversing the abdominal wall of the patient so that said distal end portion remains partially disposed proximately to said aperture so as to block entry of an abdominal organ into said aperture.

2. The method defined in claim 1 wherein said distal end portion includes an expandable element, further comprising the step of expanding said expandable element after said closure device is inserted at least partially through said opening.

3. The method defined in claim 2 wherein said expandable element is a balloon, said step of expanding including the step of inflating said balloon.

4. The method defined in claim 2, further comprising the step of severing said shaft at a point between said opening and said aperture upon completion of said step of expanding and prior to said step of closing.

5. The method defined in claim 1 wherein said step of inserting is performed prior to said step of removing, said step of inserting including the step of inserting said closure device into said sleeve so that a proximal end segment of said shaft remains outside the patient.

6. The method defined in claim 5 wherein said step of removing includes the step of grasping said proximal end segment and simultaneously pulling said sleeve from the abdominal wall of the patient.

7. The method defined in claim 1, further comprising the step of severing said shaft at a point between said opening and said aperture upon completion of said step of inserting and prior to said step of closing.

8. The method defined in claim 1 wherein a part of said shaft remains outside of said patient upon completion of said step of closing.

9. A method for use in laparoscopic surgery, comprising the steps of:
    disposing a laparoscopic trocar sleeve in an abdominal wall of a patient so that said sleeve traverses an opening in an abdominal skin surface of the patient and also traverses an underlying aperture in a peritoneum of the patient;
    providing a closure device having an elongate shaft, said closure device also having a distal end portion made of bioabsorbable material;
    inserting said closure device into said sleeve so that a proximal end segment of said shaft remains outside the patient;
    removing said sleeve from the abdominal wall of the patient;
    at least partially closing said opening subsequently to said step of removing; and
    during said steps of removing and closing and subsequently to said step of closing, maintaining said closure device at least partially traversing the abdominal wall of the patient so that said distal end portion is partially disposed proximately to said aperture so as to block entry of an abdominal organ into said aperture.

10. The method defined in claim 9 wherein said distal end portion includes an expandable element, further comprising the step of expanding said expandable element after said sleeve is removed from the abdominal wall of the patient.

11. The method defined in claim 10 wherein said expandable element is a balloon, said step of expanding including the step of inflating said balloon.

12. The method defined in claim 10, further comprising the step of severing said shaft at a point between said opening and said aperture upon completion of said step of expanding and prior to said step of closing.

13. The method defined in claim 9, further comprising the step of severing said shaft at a point between said opening and said aperture upon completion of said step of removing and prior to said step of closing.

14. The method defined in claim 9 wherein a part of said shaft remains outside of said patient upon completion of said step of closing.

15. The method defined in claim 9 wherein said step of removing includes the step of grasping said proximal end segment and simultaneously pulling said sleeve from the abdominal wall of the patient.

* * * * *